United States Patent [19]

DeBaun et al.

[11] 4,012,527

[45] * Mar. 15, 1977

[54] N,N-DIMETHYL-N'-PHENYLTHIOCARBAMYL FORMAMIDINE HYDROCHLORIDE AND ITS USE AS AN ANTI-INFLAMMATORY AGENT

[75] Inventors: Jack R. DeBaun, Sunnyvale; Ferenc M. Pallos, Walnut Creek; Eugene G. Teach, El Cerrito, all of Calif.

[73] Assignee: Stauffer Chemical Company, Westport, Conn.

[ * ] Notice: The portion of the term of this patent subsequent to May 25, 1993, has been disclaimed.

[22] Filed: Sept. 15, 1975

[21] Appl. No.: 613,673

[52] U.S. Cl. .......................... 424/323; 260/552 SC
[51] Int. Cl.$^2$ .............. A61K 31/17; C07C 127/15; C07C 127/19
[58] Field of Search ............... 260/552 SC, 564 RF; 424/323

[56] References Cited

UNITED STATES PATENTS 3,959,368   5/1976   DeBaun ...................... 260/552 SC Primary Examiner—Gerald A. Schwartz
Attorney, Agent, or Firm—Edwin H. Baker

[57] ABSTRACT

N,N-dimethyl-N'-phenylthiocarbamyl formamidine hydrochloride and its use as an anti-inflammatory agent.

2 Claims, No Drawings

N,N-DIMETHYL-N'-PHENYLTHIOCARBAMYL FORMAMIDINE HYDROCHLORIDE AND ITS USE AS AN ANTI-INFLAMMATORY AGENT

This invention relates to N,N-dimethyl-N'-phenylthiocarbamyl formamidine hydrochloride which is useful as an anti-inflammatory agent.

The compound of this invention, N,N-dimethyl-N'-phenylthiocarbamyl formamidine hydrochloride, is novel and has the following structural formula

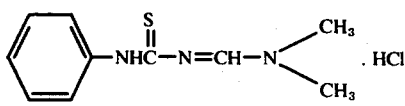

The compound of this invention can be prepared according to the teaching of the following example.

EXAMPLE

N,N-dimethyl-N'-phenylthiocarbamyl formamidine hydrochloride

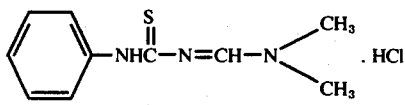

30.4 g. phenylthiourea and 23.8 g. dimethyl formamide dimethylacetal were suspended in 200 ml. of benzene with ~ 100 mg of p-toluene sulfuric acid and the mixture distilled through a 6 plate distilling column. The methanol-benzene azeotrope, b.p. 57° C, came off rapidly. After the b.p. rose to 80° C, the mixture was cooled and the product crystallized from the benzene. The yield was 37.0 g. of solid, m.p. 140°–145° C. 34.0 g. of this solid was dissolved in 100 ml. tetrahydrofuran and the desired hydrochloride salt was precipitated with an excess of ethereal hydrochloric acid. The yield was 36.4 g., m.p. 166.5°–168° C.

Hereinafter, the compound of the example will be called Compound No. 1.

Anti-Inflammatory Screening

The compound of the present invention has pharmaceutical activity especially as an anti-inflammatory agent. Anti-inflammatory acitivity is demonstrated by a test which involves the diminution of experimental edema induced in the hind paw of the rat by the injection of carrageenin.

Carrageenin injected into the foot of the rat produces an edematous condition which simulates part of the inflammatory process. Non-steroidal anti-inflammatory compounds inhibit the formation of this edema.

Methods and Procedures

The procedure used for measuring the inhibition of carrageenin-induced edema is a standard procedure well-known in the pharmaceutical art and is as follows:

Male rats (Long Evans Strain) weighing between 130-200 200 grams are used in this assay. Five rats each are used in the treatment groups and in the known standard control; whereas ten rats are used in the control edema group. Unless otherwise indicated, phenylbutazone is administered orally at 100 mg/kg to the standard control group. The edema control group is administered the vehicle which consists of 0.25% methylcellulose solution. All of the rats are fasted for at least 15 hours prior to the test. Water is available ad libitum. All of the experimental drugs are given orally and are dissolved or suspended in 0.25% methylcellulose solution. One hour after administration of the test compound, 0.05 ml of a 1% sterile solution of carrageenin is injected into the plantar tissues of the left hind paw of each rat. Three hours after carrageenin administration, the paw volumes of injected paws are then measured by means of a water displacement apparatus. The apparatus used is a modification of that described by Adamkiewicz et al., Canadian Journal of Biochemistry and Physiology, 33: 332, 1955. The amount of edema is calculated and the percent reduction of edema from control values is determined. The mean volume of edema, based on 50 determinations, is 1.25 cc with a standard deviation of 0.226 cc. A reduction in edema greater than 25% of the control value is considered significant. Based on 46 determinations, phenylbutazone produced a mean inhibition of edema of 43.8% with a standard deviation of 13.4%.

We have found that the compounds of this invention produce a significant inhibition of induced edema in rats at a dose rate of 200 mg/kg.

Table II shows the reduction in edema in the hind paw of the rat according to the above-described test procedure at 200 mg/kg unless otherwise indicated.

TABLE II

| Percent Reduction in Edema at 200 mg/kg | |
|---|---|
| Compound Number | Percent Reduction of Induced Edema |
| 1 | |

The compound of the present invention, either alone or in the form of pharmaceutical composition may be administered to an animal subject in any of a number of forms and via any of several routes. Thus, the compound or compositions thereof may be orally administered in the form of tablets, pills, capsules, or in the form of a suspension. The compound may also be administered parenterally in the form of an injectable solution or suspension. The compound or compositions thereof may also be administered topically, in the form of an ointment, or rectally, in the form of a suppository.

When orally administering the compound or compositions, use can be made of a tablet, pill or capsule consisting entirely of the compound, although ordinarily, a composition comprising an effective amount of the compound and varying amounts of one or more physiologically inert materials such as carriers, vehicles, binders and the like will be used. Additionally, the compound may be orally administered in the form of a suspension thereof in a suitable vehicle such as a syrup.

When parenterally administering the compound or compositions, use may be made of a parenteral solution or suspension of the compound in a suitable solvent or suspension medium.

The compound of the present invention may also be administered rectally in the form of a suppository comprising an effective amount of the desired compound and a suitable vehicle such as petroleum jelly.

Finally, the compound of the present invention may be applied topically in the form of an ointment, salve, cream or lotion comprising an effective amount of the compound and a suitable vehicle such as petroleum jelly, etc.

We claim:

1. N,N-dimethyl-N'-phenylthiocarbamyl formamidine hydrochloride.

2. A method of treatment of an inflammatory condition in a mammal comprising administering to said mammal a therapeutically effective amount of N,N-dimethyl-N'-phenylthiocarbamyl formamidine hydrochloride.

* * * * *